US006183220B1

(12) United States Patent
Ohara et al.

(10) Patent No.: US 6,183,220 B1
(45) Date of Patent: Feb. 6, 2001

(54) CENTRIFUGAL BLOOD PUMP

(75) Inventors: Yasuhisa Ohara, Nagoya (JP);
Yoshiyuki Takami, Houston, TX (US);
Goro Otsuka, Houston, TX (US);
Yukihiko Nose, Houston, TX (US);
Kenzo Makinouchi; Michihiro Yokokawa, both of Gamo-gun (JP)

(73) Assignees: Kyocera Corporation, Kyoto (JP);
Baylor College of Medicine, Houston, TX (US)

( * ) Notice: Under 35 U.S.C. 154(b), the term of this patent shall be extended for 0 days.

(21) Appl. No.: 09/258,644

(22) Filed: Feb. 26, 1999

(30) Foreign Application Priority Data

Feb. 27, 1998 (JP) .................................. 10-047019

(51) Int. Cl.⁷ .................................................. F04B 17/00
(52) U.S. Cl. ............................................. 417/420; 415/206
(58) Field of Search .............................. 417/420, 423.7, 417/423.12; 604/131; 415/206, 900

(56) References Cited

U.S. PATENT DOCUMENTS

| 4,984,972 | | 1/1991 | Clausen et al. . | |
| 5,017,103 | * | 5/1991 | Dahl | 417/420 |
| 5,290,236 | * | 3/1994 | Mathewson | 604/131 |
| 5,360,317 | * | 11/1994 | Clause et al. | 415/206 |
| 5,399,074 | | 3/1995 | Nose et al. . | |
| 5,575,630 | * | 11/1996 | Nakazawa et al. | 417/420 |
| 5,658,136 | * | 8/1997 | Mendler | 417/420 |
| 5,803,720 | * | 9/1998 | Ohara et al. | 417/420 |
| 5,863,179 | * | 1/1999 | Westphal et al. | 415/206 |

* cited by examiner

Primary Examiner—Philip H. Leung
Assistant Examiner—Leonid Fastovsky
(74) Attorney, Agent, or Firm—Hogan & Hartson, LLP

(57) ABSTRACT

The present invention provides a blood pump capable of substantially completely preventing thrombus from attaching to the inner bottom portion of the casing without lowering the anti-hemolytic characteristic of blood. A centrifugal blood pump in accordance with the present invention comprises a pump casing, a suction inlet disposed at the central portion on the upper side of the casing, a delivery outlet disposed at the bottom peripheral portion of the casing, a main impeller (D in diameter) for forming a centrifugal flow of blood supplied from the suction inlet in the range from the central portion to the peripheral portion to feed the blood to the delivery outlet, wherein the main impeller is provided with an stirring impeller, the surface of which is provided with one or more stirring elements (L in entire length) having the shape of a fin or a groove, and the dimensions of the stirring elements are determined to satisfy inequality (1): $0.43 < L/D < 1.30$ and inequality (2) $0.03 < S/A < 0.21$, where S is the surface area of the blood contact surfaces of the stirring elements.

5 Claims, 8 Drawing Sheets

CENTRIFUGAL BLOOD PUMP

FIELD OF THE INVENTION

The present invention relates to a blood pump used for artificial auxiliary hearts and heart-lung machines, and more particularly to a blood pump capable of preventing thrombus from attaching to the interior thereof.

PRIOR ART

Conventionally, a centrifugal pump has been used as a blood pump. The centrifugal pump comprises a conical impeller for generating a centrifugal flow inside the housing thereof, a suction inlet, through which blood is, drawn, disposed near the rotation center portion of the impeller, a delivery outlet, through which blood pressurized by the impeller is discharged from the peripheral portion of the impeller, a motor disposed outside the casing to rotate the impeller, and a seal formed between the casing and the rotation shaft of the impeller. This pump is called a sealed type wherein the interior of the casing is maintained water-tight by sealing.

Furthermore, U.S. Pat. No. 4,984,972 has proposed a seal-less type blood pump, wherein the impeller is rotated in a non-contacting condition by a rotating magnetic field outside the casing. The impeller is provided with magnetic material assigned to the magnetic field, and both ends of its rotation shaft are supported by pivot bearings attached inside the casing.

In the case of the above sealed type centrifugal blood pump, it is difficult to completely seal the clearance between the rotation shaft and the casing. As a result, the blood is apt to be clotted at this sealed portion, generating the so-called thrombus. Paticularly, The thrombus may grow in areas inside the casing where the flow rate of blood is dropped.

Furthermore, the seal-less type blood pump may also cause thrombus at the inner bottom portion of the casing on the opposite side of the suction inlet, although the pump has no sealing portion for the rotor of the impeller. In order to solve this problem, U.S. Pat. No. 5,399,074 proposes a blood pump of the seal-less type which is provided with through holes penetrated through the impeller up to the bottom side, or auxiliary vanes (or secondary vanes) projected from the bottom surface of the impeller, then enhancing the fluidity of the blood on the bottom of the casing.

However, no sufficient blood fluidity was obtained by just forming the through holes in the seal-less pump, and thrombus was unable to be prevented.

Furthermore, in the case when the auxiliary vanes were provided, thrombus was able to be prevented. However, this caused a problem of generating hemolysis, that is, hemocytes in blood passed through the pump were apt to be destructed. Hemolysis herein means a characteristic or an extent of hemocytes being apt to be destructed by the auxiliary vanes. Blood flows slowly and is apt to stay at the inner bottom portion of the casing in the blood pump, whereby thrombus is apt to be caused. When the auxiliary vanes are used, thrombus can be prevented by the stirring force of the auxiliary vanes. However, hemocytes are apt to be destructed at the same time.

SUMMARY OF THE INVENTION

In order to solve the above-mentioned problems peculiar to the above-mentioned centrifugal blood pumps, an object of the present invention is to provide a blood pump capable of substantially completely preventing thrombus from attaching to the inner bottom portion of the casing thereof without deteriorating the anti-hemolytic characteristic of blood.

In the present invention, one or more stirring elements having the shape of a fin or a groove are formed on the bottom of the main impeller facing the inner bottom surface of the pump casing. In the invention, the dimensions, shape and positions of the fins or grooves used as the stirring elements are determined to completely prevent thrombus from attaching to the inner bottom portion of the casing without deteriorating the anti-hemolytic characteristic of blood.

To attain this purpose, the dimensions, shape and positions of the stirring elements are defined using parameters of a ratio L/D of the entire length L of the fins or grooves to the diameter D of the impeller, and a ratio S/A of the surface area S of the blood contact surfaces of the fins or grooves to the projected area A of the impeller. The entire length L of the fins or grooves conforming to the shape of the impeller and the surface area S of the blood contact surfaces of the fins or grooves are determined in accordance with the parameters.

These parameters can be chosen to be in ranges where the normal anti-hemolytic characteristic of blood and nonattachment of thrombus are maintained, as follows.

$$0.43 < L/D < 1.30 \tag{1}$$

and, $$0.03 < S/A < 0.21 \tag{2}$$

The two inequalities (1) and (2) relates to adequate force for stirring blood in the clearance between the bottom surface of the impeller and the inner bottom of the casing. If parameters L/D and S/A are both smaller than the lower limits in the ranges of the inequalities (1) and (2), respectively, the force stirring blood by the fins or grooves used as the stirring elements is so weak that thrombus is apt to attach to the inner bottom portion of the casing. If the parameters are larger than the higher limits in the range, the stirring force is so excessive that the amount of hemolysis increases because of destructed hemocytes, whereby the anti-hemolytic characteristic of blood is impaired.

BRIEF DESCRIPTION OF THE DRAWINGS

The present invention will be described below in further detail referring to the accompanying drawings, in which.

DETAILED DESCRIPTION OF THE INVENTION

A centrifugal blood pump in the present invention comprises a pump casing, a suction inlet disposed at the central portion on the upper side of the casing, a delivery outlet disposed at the bottom peripheral portion of the casing, a main impeller rotated inside the casing to form a centrifugal flow of blood supplied from the suction inlet in the range from the central portion to the peripheral portion of the casing and to feed the blood to the delivery outlet, wherein the main impeller is provided with an stirring impeller on the bottom side of the casing so as to be coaxial with each other, and the surface of the stirring impeller is provided with one or more stirring elements having the shape of a fin or a groove extending in the approximately radial direction from the center side thereof.

Figure 1A:
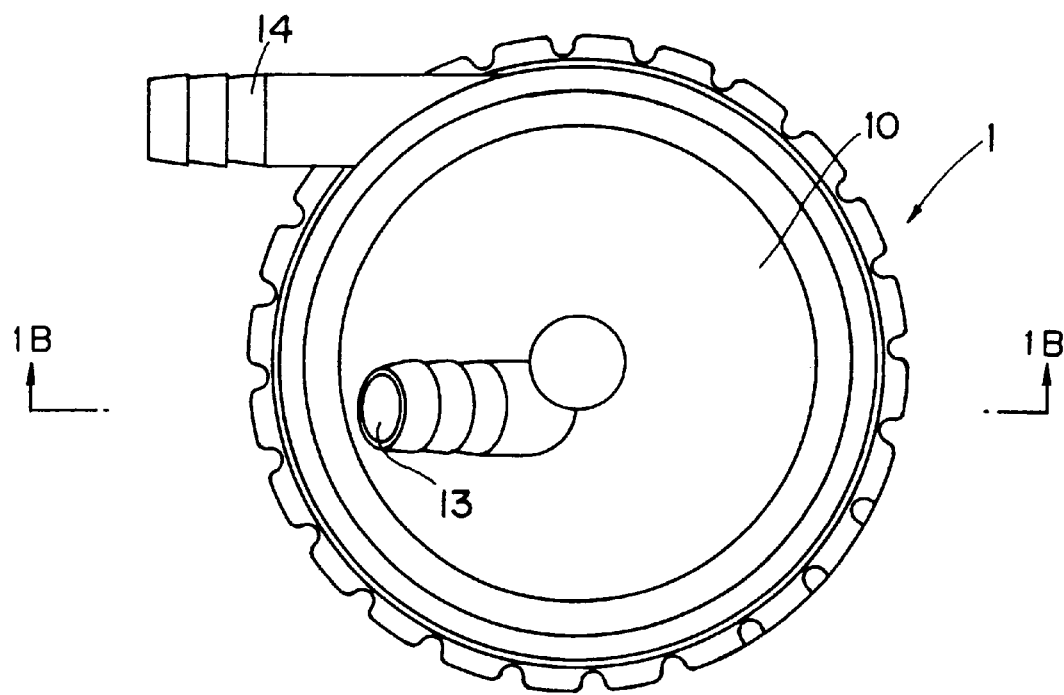
FIG. 1A is a top view showing a centrifugal blood pump.
Figure 1B:
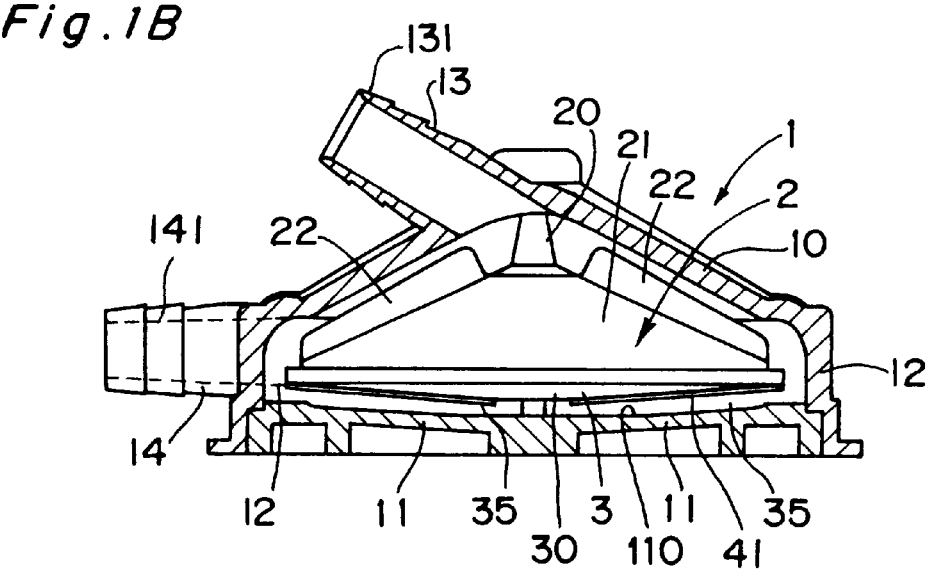
FIG. 1B is a partially sectional view showing the centrifugal blood pump in accordance with an embodiment of the present invention.
Figure 2:
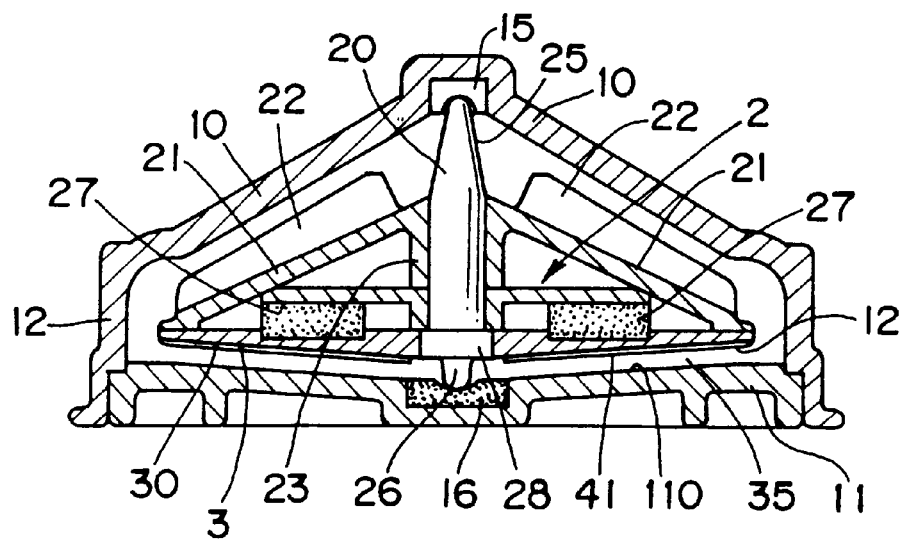
FIG. 2 is a sectional view showing the centrifugal blood pump in accordance with the embodiment of the present invention.

FIGS. 1A, 1B and 2 show an example of this kind of centrifugal blood pump 1. The internal configuration of a pump casing 10 is a watertight container having a circular shape in the lateral cross-section thereof and a conical shape in the vertical cross-section thereof.

A suction inlet 13 is provided near the apex of the conical shape of the pump casing 10, and a tube connection fitting 131 is integrally secured thereto. On the other hand, a delivery outlet 14 is provided on the peripheral. side 12 of the bottom portion of the pump casing 10, and a tube connection fitting 141 is integrally secured thereto.

Referring to these figures, in the interior of the pump casing 10 are provided a pivot bearing 15 at the apex of the conical shape and a pivot bearing 16 at the inner central portion of the bottom portion 11 of the conical shape, and the rotation shaft 20 of a main impeller 2 is rotatably supported between the two pivot bearings. The main impeller 2 comprises plural vanes 22 raised and secured to the outer peripheral surface of the conical rotor 21 thereof. The vanes 22 are projected toward the inner surface of the pump casing 10.

As the main impeller 2 rotates, the plural vanes 22 which are rotating cause centrifugal force to move the blood centrifugally in the cavity between the outer surface of the peripheral body of the rotor 21 of the main impeller 2 and the inner peripheral surface of the casing 10. Accordingly, the rotating vanes 22 take out blood by suction from the suction inlet 13 and feeds blood under pressure to the delivery outlet 14 passing through the said cavity.

Rotation of the impeller is driven by ferromagnetic bodies, for example, magnets 27, secured to the interior of the main impeller 2, which follows rotating magnetic field by produced by electromagnetic coils or rotating magnets 61 on external rotor 6 (see FIG. 8) arranged outside the casing.

In the pump of the present invention, a disc-shaped stirring impeller 3 is fixed to the bottom side of the main impeller 2, facing the inner bottom surface of the casing 10, and one or more fins 41 or grooves 42 extend in the approximately radial direction from the central side of the stirring impeller 3 as stirring elements on the surface of the stirring impeller 3 as shown in FIG. 2.

The diameter of the stirring impeller 3 is nearly equal to that of the main impeller 2. The center hole 37 of the stirring impeller 3 is fit on the outer periphery of the stepped portion 28 formed on the rotation shaft 20 to interact with interior surface 23 of the main impeller 2. The outer periphery of the stirring impeller 3 is joined to that of the main impeller 2 so as to be secured to each other.

As the main impeller 2 rotates, these fins 41 or grooves 42 as stirring elements can agitate the blood present in the clearance 35 between the stirring impeller 3 and the inner surface 110 of the bottom portion 11 of the pump casing 10.

Figure 3A:
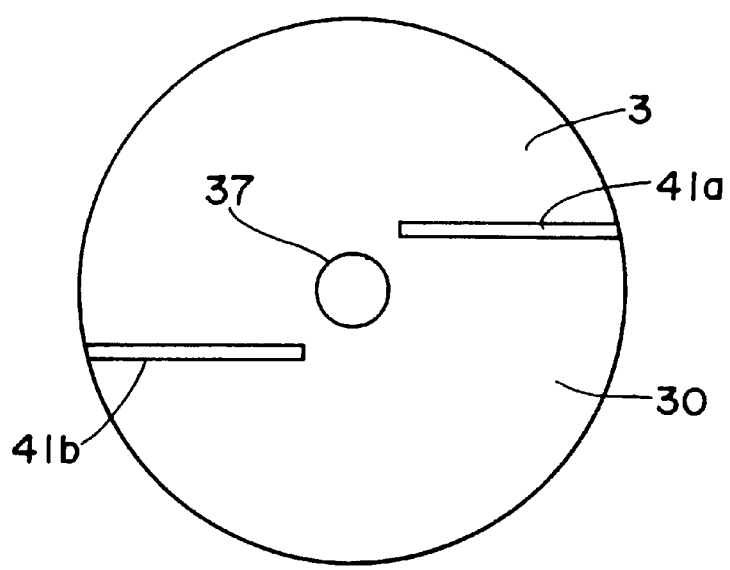
FIG. 3A is a bottom view showing the stirring impeller of the centrifugal blood pump in accordance with the embodiment of the present invention.
Figure 3B:
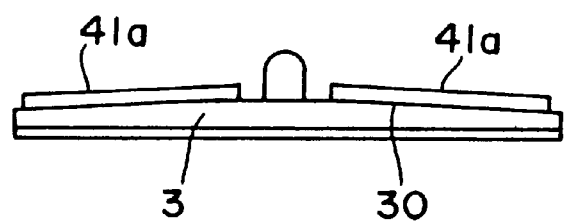
FIG. 3B is a side view showing the stirring impeller of the centrifugal blood pump.
Figure 6A:
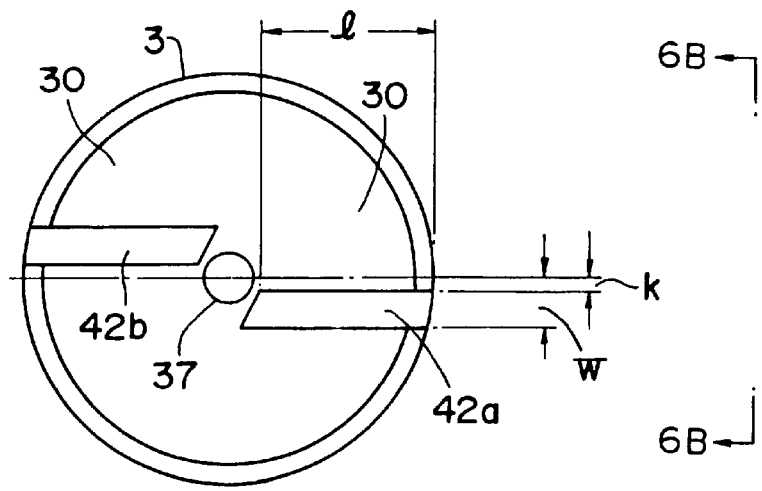
FIGS. 6A and 6B are a bottom view and a side view showing the stirring impeller of the centrifugal blood pump in accordance with the embodiment of the present invention, respectively, showing the positions of the grooves on the surface of the stirring impeller.
Figure 6B:
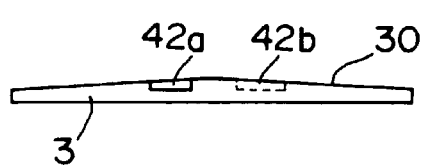

The fins 41 or grooves 42 are rectangular in cross-section in a typical case. FIGS. 3A and 3B show an example of a stirring impeller 3 having two sectionally rectangular fins 41. FIGS. 6A and 6B show an example of the stirring impeller 3 provided with two sectionally rectangular grooves 42.

Figure 4A:
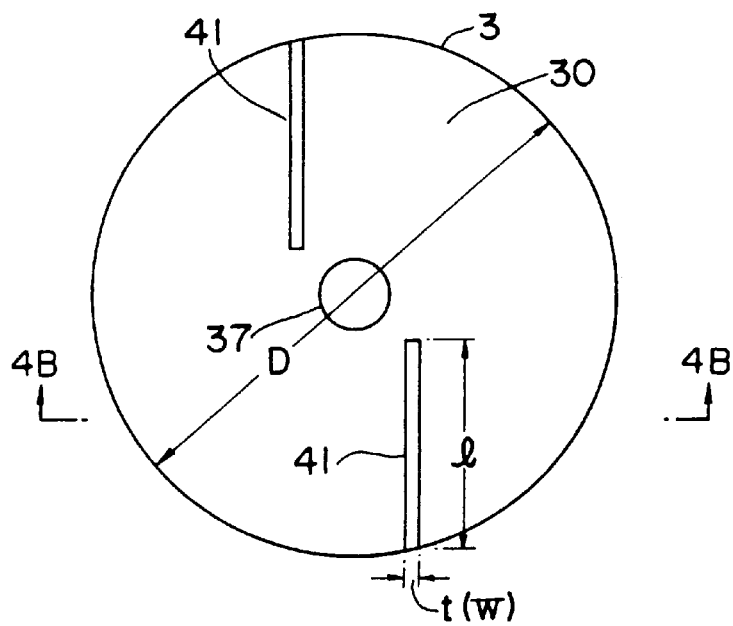
FIG. 4A is a bottom view showing the bottom side of the stirring impeller in the centrifugal blood pump according to the embodiment of the present invention.
Figure 4B:
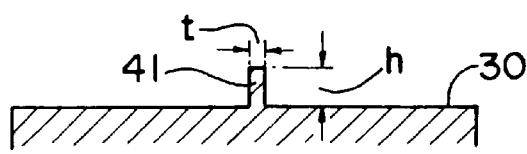
FIGS. 4B to 4G are sectional views showing various shapes of fins and grooves formed on the bottom surface of the stirring impeller.
Figure 4C:
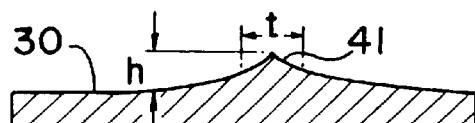
Figure 4D:
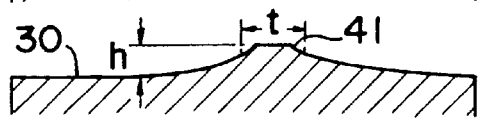

Instead of the rectangular shape in cross-section (FIG. 4B), a shape having a pointed top and gradual bottom portions in cross-section (FIG. 4C), or a trapezoidal shape having gradual bottom portions (FIG. 4D) can be used for the fins 41.

Figure 4E:
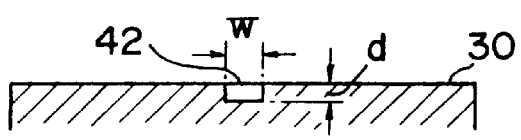
Figure 4F:
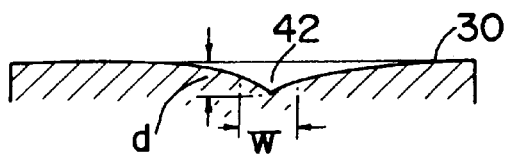
Figure 4G:
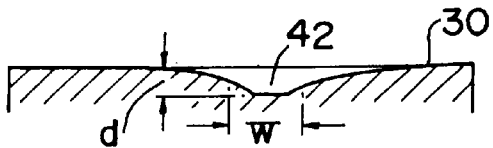

Furthermore, instead of the rectangular shape in cross-section (FIG. 4E), a shape having gradual bottom portions in cross-section (FIG. 4F, FIG. 4G) can be used for the groove 42.

In the present invention, in order to prevent the generation of thrombus and the deterioration of the anti-hemolytic characteristic of blood because of the agitation of blood, the fins 41 or the groove 42 are requested to satisfy inequalities (1) and (2).

$$0.43 < L/D < 1.30 \tag{1}$$

and, $$0.03 < S/A < 0.21 \tag{2}$$

In the parameter L/D of the inequality (1), D is the diameter of the stirring impeller, and L is the entire length of the fins 41 or the grooves 42.

In the case where the number n of fins 41 or n grooves 42 are formed on the stirring impeller, the entire length L of the fins 41 or the grooves 42 in the parameter L/D, is the sum total of the lengths l of all the fins 41 or grooves 42, whereby L is represented by L=nl.

In the parameter S/A of the inequality (2), A is a projected area ($=\pi D^2/4$) of the impeller which is projected on a plane perpendicular to the rotation shaft.

S is the surface area of the blood contact surfaces of the fins 41 or the grooves 42. In the case of n fins 41 having a thickness of t, a height of h and a length of l as shown in FIGS. 4A to 4G (n=2 as an example), the contact surface area S of the two fins 41 is represented by;

$$S = n(tl + 2th + 2hl).$$

In the case of n grooves 42 having a depth of d, a width of w and a length of l, the contact surface area S of the grooves 42 is represented by;

$$S = n(wl + 2wd + 2dl).$$

The above parameter inequalities (1) and (2) are applicable to a variety of normal-sized blood pumps. In particular, these inequalities are preferably applicable to blood pumps wherein the diameter D of the impeller 2 is in the range of 20 to 100 mm, the clearance between the inner surface 110 of the bottom portion 11 of the pump casing 10 and the surface 30 of the stirring impeller 3 is in the range of 1 to 20 mm, and the rotation speed T of the impeller 3 is in the range of 1000 to 6000 rpm.

Figure 7A:
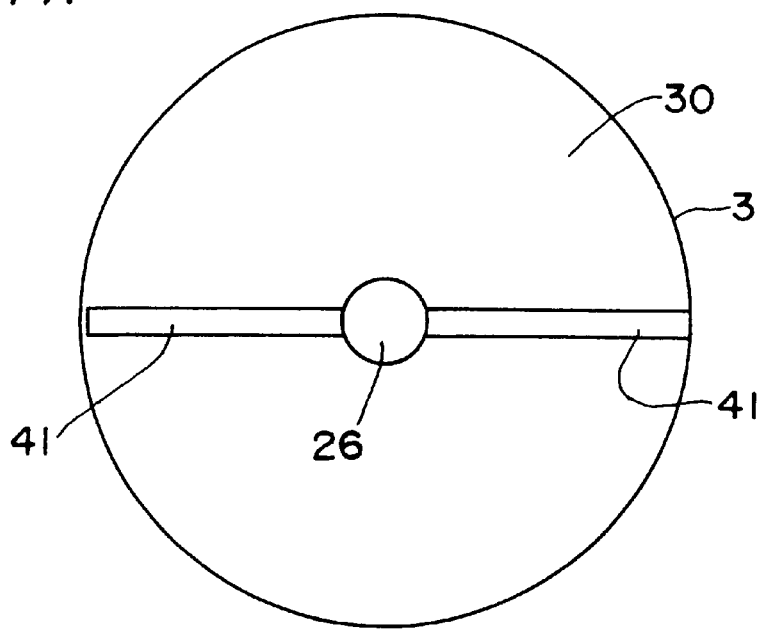
FIG. 7A is a bottom view showing the stirring impeller of the centrifugal blood pump in accordance with another embodiment of the present invention.
Figure 7B:
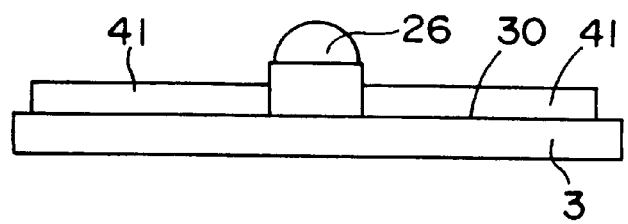
FIGS. 7B to 7D are side views of the stirring impeller.
Figure 7C:
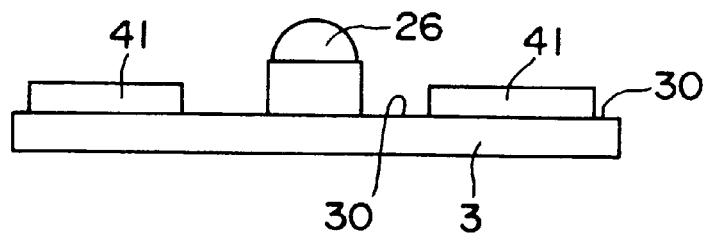
Figure 7D:
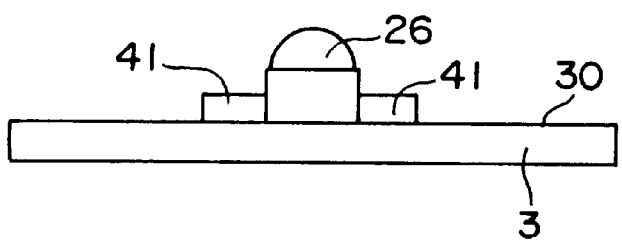

As other examples of the shapes of the stirring impeller mentioned above, the stirring impeller 3, the fins 41, 41 as the stirring elements and the pivot 26 are integrated to form easily an stirring impeller as shown in FIGS. 7A and 7B. In the example shown in FIG. 7A, the fins 41, 41 making contact with the pivot 26 located at the pointed end of the rotation shaft 20 are extended to the outer periphery of the stirring impeller 3. In the example shown in FIG. 7C, the fins 41, 41 are formed to have a clearance from the pivot 26 extending to the outer periphery of the stirring impeller 3. FIG. 7D shows that the fins 41, 41 are formed to make contact with the pivot 26, being short in length.

In these examples, the fins 41, 41 are integrated with the pivot 26 to prevent blood from staying at the clearance between the fins 41, 41 and the pivot 26, or the fins 41, 41 are changed in length and position to prevent hemolysis from generating in this area.

EMBODIMENTS

In order to optimize stirring impellers 3 having the fins 41 and the stirring impeller 3 having the grooves 42 to prevent thrombus from generating and to prevent the antihemolytic characteristic of blood from lowering, tests were conducted in accordance with the following processes.

Figure 5A:
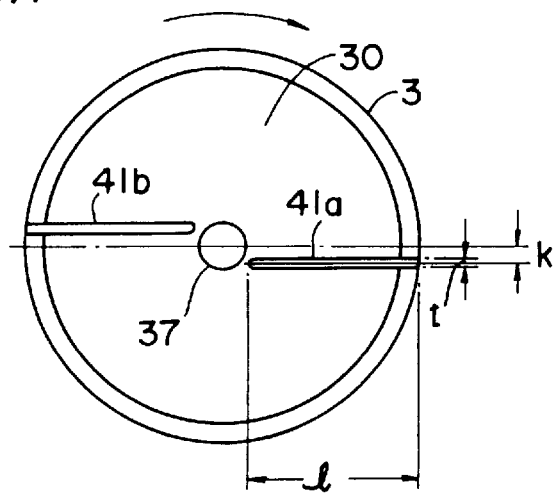
FIGS. 5A to 5C are bottom views showing the stirring impeller of the centrifugal blood pump in accordance with the embodiment of the present invention, showing the positions of the fins on the surface of the stirring impeller.
Figure 5B:
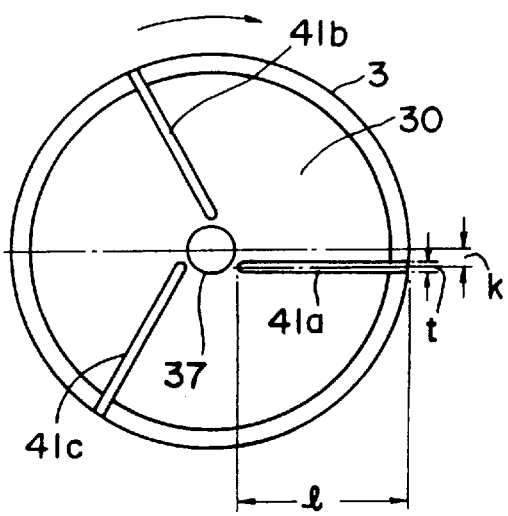
Figure 5C:
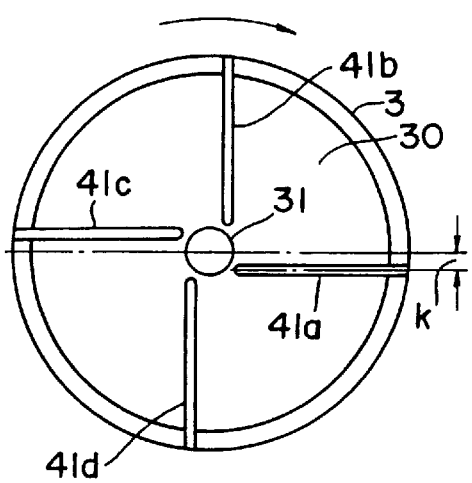

The impellers 3 having the fins 41 were produced so as to have the following dimensions: the diameter D of the impeller=65 mm, the length l of the fin 41=28 mm, the thickness t=1.6 mm, and the height h=1.0 mm. The number n of the fins 41 was 2 to 4. The outside shapes of these impellers 3 are shown in FIGS. 5A to 5C.

Figure 6C:
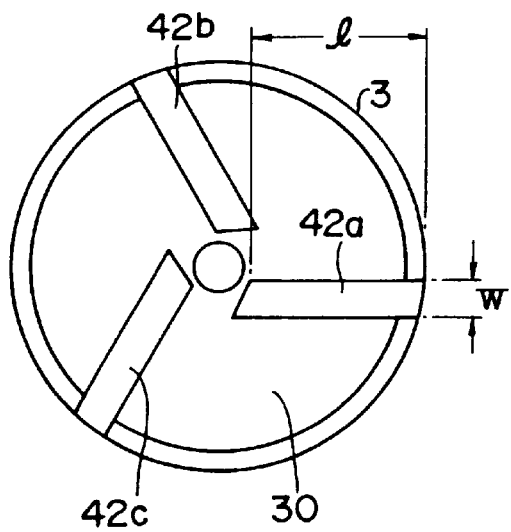
FIGS. 6C and 6D are bottom views of the stirring impeller of the centrifugal blood pump having three grooves and four grooves, respectively, in accordance with other embodiments of the present invention.
Figure 6D:
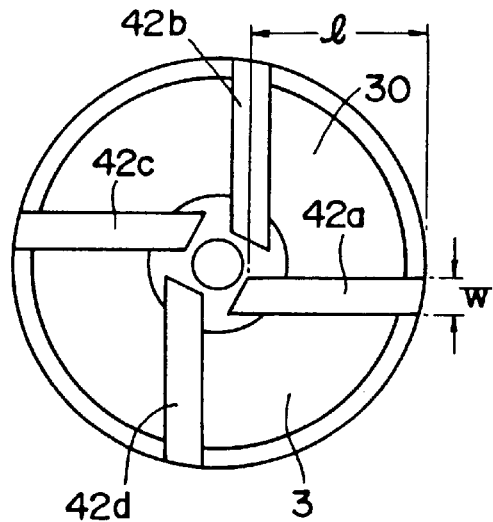

The impellers 3 having the grooves 42 were produced having the following dimensions: the diameter D of the impeller=65 mm, the length l of the groove=28 mm, the width w thereof=0.6 mm, and the depth d thereof=0.08 mm. The number n of the grooves 42 was 2 to 4. The outside shapes of these impellers 3 are shown in FIGS. 6A, 6C and 6D.

The parameters L/D and S/A for the impellers having the fins and the impellers having the grooves were obtained and indicated in TABLES 1 and 2.

TABLE 1

| n of fin | 0 | 1 | 2 | 3 | 4 |
|---|---|---|---|---|---|
| L/D | 0 | 0.43 | 0.86 | 1.29 | 1.72 |
| S/A | 0 | 0.031 | 0.063 | 0.094 | 0.125 |

TABLE 2

| n of groves | 0 | 1 | 2 | 3 | 4 |
|---|---|---|---|---|---|
| L/D | 0 | 0.43 | 0.86 | 1.29 | 1.72 |
| S/A | 0 | 0.067 | 0.134 | 0.201 | 0.268 |

The stirring impellers having the fins and the impellers having the grooves were installed in the main impeller of the centrifugal blood pump and subjected to thrombus and hemolysis tests.

First, an animal experiment was carried out for the thrombus test by using a cow of 3 to 4 months old. Blood is taken out of the apex of the left ventricle of the cowl's heart, and fed to its descending aorta under pressure by a blood pump installed on a special-purpose saddle on the back. Blood processing from taking out blood to feeding blood was carried out by using the blood pump through a polyvinyl chloride tube of ⅜ inches in diameter.

The experiment was conducted continuously while replacing blood pumps every 24 hours. During the test, Heparin anticoagulant was supplied continuously into the vein of the cow to control the value of Activated Clotting Time (ACT) in the range of 150 to 200, thereby to control the anticoagulant characteristic of blood.

After operating the pump, the blood pumps were cleaned with a physiological saline solution to observe the inner surface 110 of the bottom portion 11 of the casing 10 and the surface of the stirring impeller 3, and then the attachment extent of clotted blood was evaluated by attached area of blood on the bottom surface.

TABLE 3

| | | area covered by the clotted blood (mm$^2$) | | | |
|---|---|---|---|---|---|
| n of fins | | 0 | 2 | 3 | 4 |
| Test | 1 | 80 | 6 | 5 | 15 |
| No. | 2 | 100 | 0 | 3 | 9 |
| | 3 | 180 | 6 | 3 | 19 |
| mean | | 120 | 4 | 4 | 14 |

TABLE 4

| | | area covered by the clotted blood (mm$^2$) | | | |
|---|---|---|---|---|---|
| n of grooves | | 0 | 2 | 3 | 4 |
| Test | 1 | 80 | 12 | 6 | 25 |
| No. | 2 | 100 | 8 | 4 | 42 |
| | 3 | 180 | 10 | 3 | 23 |
| mean | | 120 | 10 | 4 | 30 |

The results of the test were summarized in TABLES 3 and 4. Some clotted portions were observed at the central areas on the surfaces of all the stirring impellers. In particular, in the case of the stirring impellers without the fins 41 or the grooves 42, clotted surface areas became very large. In the case of the stirring impellers having two or three fins 41 or grooves 42, the clotted surface areas became small. However, four fins 41 or grooves 42 increased the clotted surface areas.

Next, the hemolysis test was conducted by using the above-mentioned pumps in the following conditions to examine the extent of damage incurred by blood cells due to the impellers during operating the pump, that is, to examine the numerical index of hemolysis (NIH).

Figure 8:
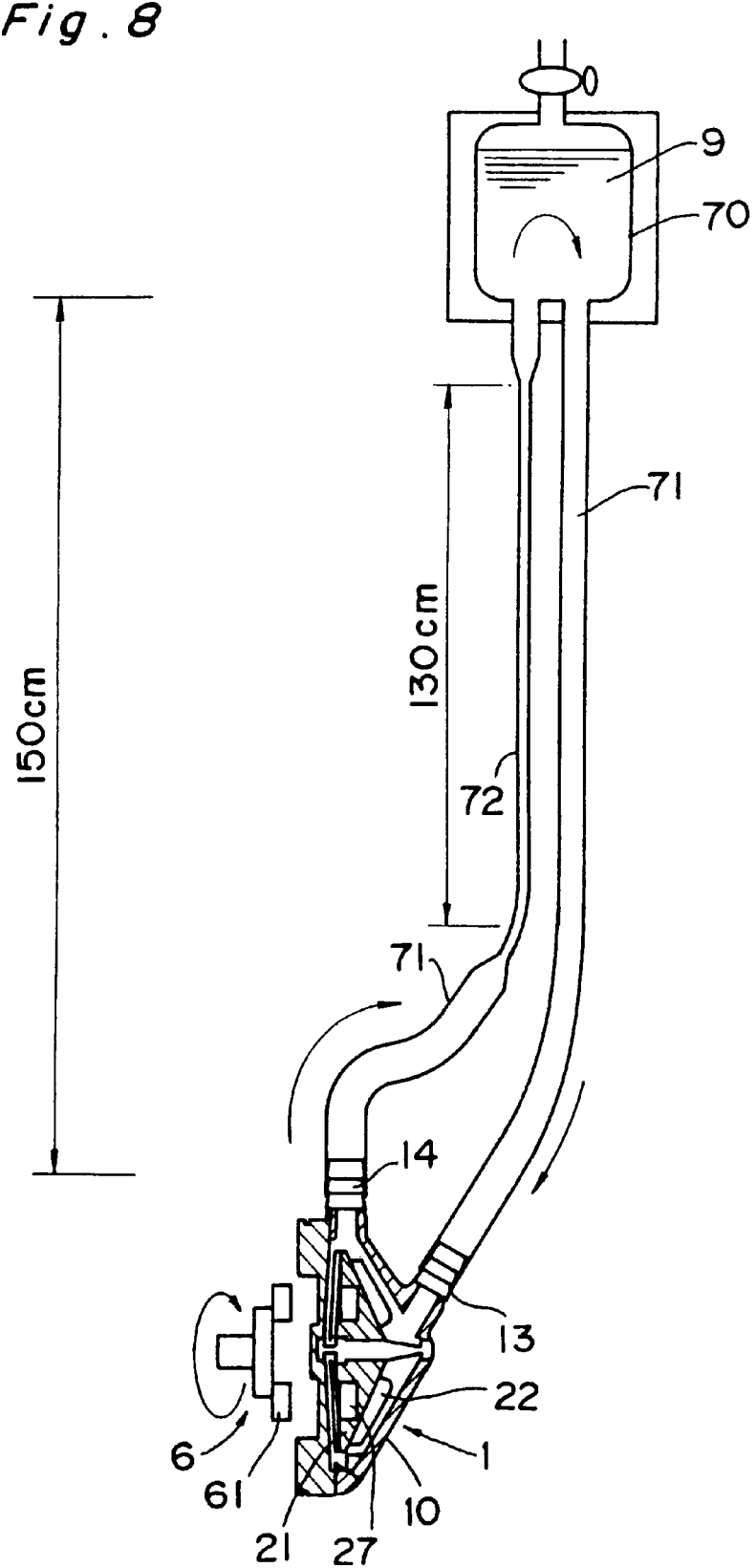
FIG. 8 is a view showing a blood circulation circuit comprising a centrifugal blood pump and a blood container used for a hemolysis test according to the embodiment of the present invention.

The blood under experiment was adjusted by adding a 10% aqueous solution of sodium citrate as an anticoagulant to the cow's blood so that the aqueous solution has 7 vol % in the mixture (hematocrit (Ht)=0.48). The test was carried out in the conditions wherein the flow rate (Q) of the blood was 5 l/min, and the total head was 350 mmHg. FIG. 8 shows a circuit for blood circulation. The suction inlet 13 and the delivery outlet 14 were connected to a container 70 positioned higher than a blood pump 1 via polyvinyl chloride hoses 72, and blood 9 was circulated between the container 70 and the pump 1. During the circulation, the temperature of the blood was maintained at 25±3° C.

During the test, the blood was sampled 2 ml at a time before the start of pump operation, and 10 and 20 minutes after starting the test. The concentration f-Hb of free hemoglobin in blood was determined by the Flourene technique, and the numerical index of hemolysis (NIH) was obtained by using the following equation.

$$NIH = \Delta[f\text{-}Hb(1-Ht)]/\Delta N$$

where Ht is hematocrit, and N is a circulation number represented by N=Q×t/Vo, Q being the flow rate of the blood, Vo being the total volume of the blood in the blood circulation circuit, and t circulation time.

The numerical index of hemolysis (NIH) itself greatly depends on the history of the blood and the individual characteristics of the cow, i.e., the supplier of the blood. For this reason, the numerical index of hemolysis of the same blood was determined by using the commercially available centrifugal blood pump of type BP80 made by Medtronic Inc.

The numerical index of hemolysis (NIH) obtained in each pump by the above-mentioned experiment, was compared with that measured by the BP80, and the ratio of the two NIH data was defined as the relative numerical index of hemolysis. The results of the hemolysis test were shown in TABLE 4, and FIGS. 9A and 9B.

Figure 9A:
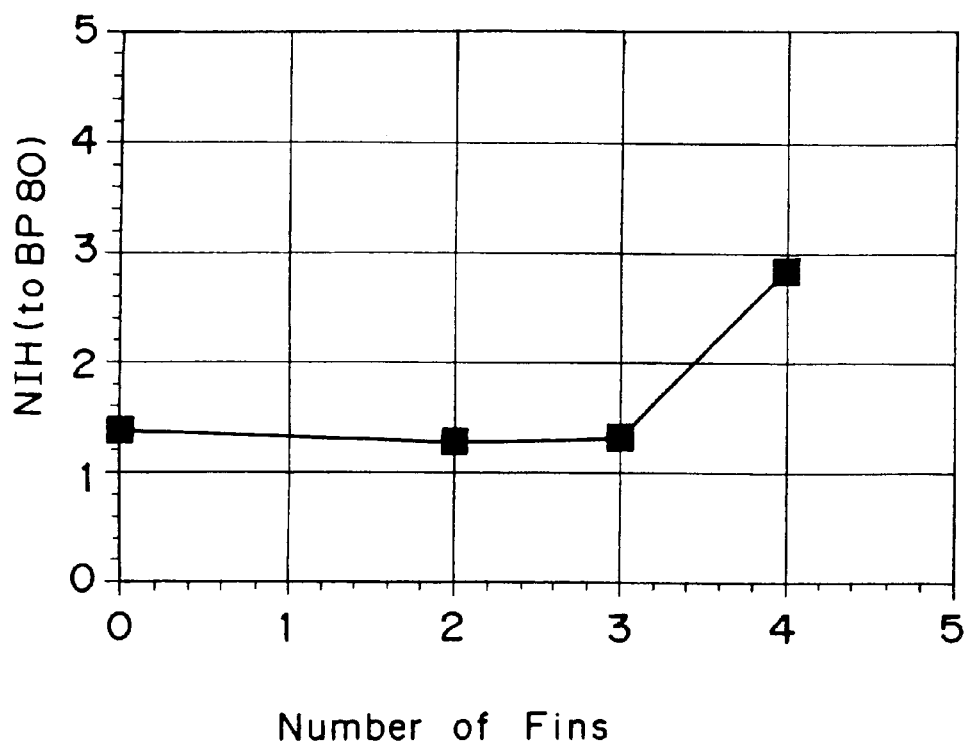
FIG. 9A is a graph showing the relationship between the relative numeral index of hemolysis obtained by the hemolysis test and the number (n) of fins in accordance with the embodiment of the present invention; and, FIG. 9B is a graph showing the relationship between the relative numeral index of hemolysis obtained by the hemolysis test and the number (n) of grooves in accordance with the same embodiment.
Figure 9B:
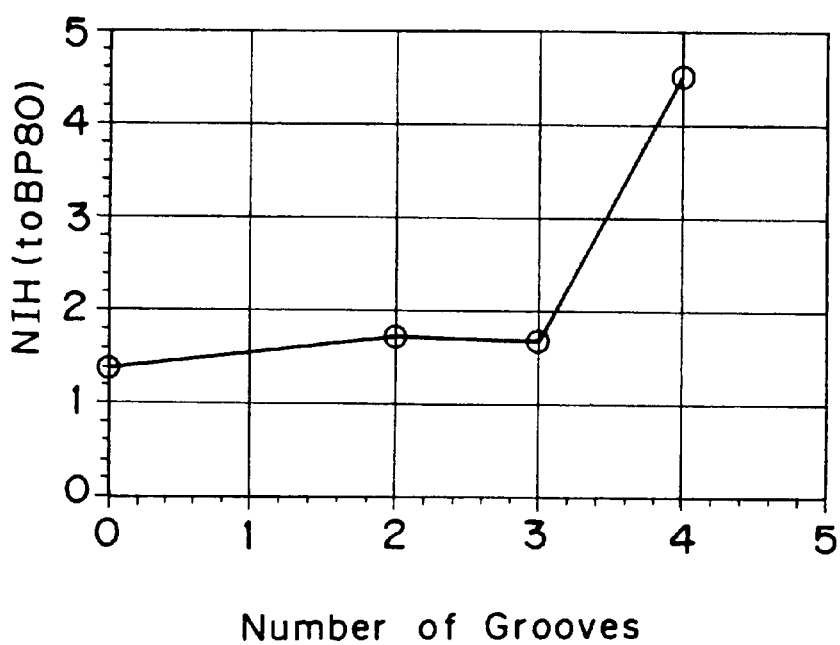

From the results shown in FIGS. 9A and 9B, it is seen that the destruction of hemocytes in blood is apt to proceed, i.e., that the anti-hemolytic characteristic in blood deteriorates in the case where the number n of the fins or the grooves is 4.

As described above, the number n of the above-mentioned fins 41 or grooves 42 is required to be in the range of 1 to 3. In accordance with the relationships indicated in TABLES 1 and 2, it is found that the pump effectively prevent the blood in being supplied from clotting and hemolyzing in the blood pump, as the two inequalities (1) and (2) are satisfied.

In the case of using the fins 41 in particular, it is desired that the following inequality (3) should be satisfied;

$$0.03 < S/A < 0.10 \tag{3}$$

Furthermore, in the case of using the grooves 42, it is desired that the following inequality (4) should be satisfied;

$$0.06 < S/A < 0.21 \tag{4}$$

We claim:

1. A centrifugal blood pump comprising a pump casing, a suction inlet disposed at the central portion on the upper side of the casing, a delivery outlet disposed at the bottom peripheral portion of the casing, a main impeller rotated inside the casing to form a centrifugal flow of blood supplied from the suction inlet to the peripheral portion of the casing and to feed the blood to the delivery outlet, wherein the main impeller is provided with an stirring impeller coaxially facing the inner bottom side to the casing, and the surface of the stirring impeller is provided with one or more stirring elements having the shape of a fin or a groove extending in the approximately radial direction from the center side thereof, and, the stirring elements satisfy the following inequalities (1) and (2);

$$0.43 < L/D < 1.30 \tag{1}$$

and, $$0.03 < S/A < 0.21 \tag{2},$$

where D is the diameter of the impeller, L is the entire length of the fins or the grooves, A is a projected area of the impeller being projected on a plane perpendicular to a rotation shaft of the impeller, and S is the surface area of the blood contact surfaces of the stirring elements.

2. The centrifugal blood pump according to claim 1, wherein the stirring elements are fins and satisfy the following inequality (3);

$$0.03 < S/A < 0.10 \tag{3}.$$

3. The centrifugal blood pump according to claim 1, wherein the stirring elements are grooves and satisfy the following inequality (4);

$$0.06 < S/A < 0.21 \tag{4}.$$

4. The centrifugal blood pump according to claim 1, wherein the number of the stirring elements is 1 to 3.

5. The centrifugal blood pump according to claim 1, wherein both ends of the main impeller are pivotally supported inside the casing and rotated by an external rotating magnetic field.

* * * * *